United States Patent [19]

Birkenstock et al.

[11] 4,407,733

[45] Oct. 4, 1983

[54] SUPPORTED CATALYSTS AND PROCESS FOR THEIR PREPARATION

[75] Inventors: Udo Birkenstock, Ratingen; Herbert Schmidt, Leverkusen, both of Fed. Rep. of Germany

[73] Assignee: Bayer Aktiengesellschaft, Leverkusen, Fed. Rep. of Germany

[21] Appl. No.: 284,752

[22] Filed: Jul. 20, 1981

Related U.S. Application Data

[63] Continuation of Ser. No. 66,976, Aug. 16, 1979.

[30] Foreign Application Priority Data

Nov. 11, 1978 [DE] Fed. Rep. of Germany ....... 2848978

[51] Int. Cl.$^3$ ........................ B01J 23/58; B01J 23/78; B01J 23/89
[52] U.S. Cl. .................................... 502/174; 502/208; 502/240; 502/300; 502/302; 502/305; 502/324; 502/332; 502/330; 502/527
[58] Field of Search ........... 252/435, 443, 454, 455 R, 252/457, 462, 463, 466 PT, 467, 468, 470, 471, 473, 474, 475, 476, 477 R

[56] References Cited

U.S. PATENT DOCUMENTS

| | | | |
|---|---|---|---|
| 3,036,137 | 5/1962 | Challis et al. | 585/259 |
| 3,116,342 | 12/1963 | Robinson et al. | 585/260 |
| 3,839,225 | 10/1974 | Acres | 252/465 |
| 4,094,821 | 6/1978 | McVicker et al. | 252/473 X |
| 4,171,329 | 10/1979 | Koniz et al. | 252/463 X |

FOREIGN PATENT DOCUMENTS 1944933 9/1969 Fed. Rep. of Germany.

*Primary Examiner*—W. J. Shine
*Attorney, Agent, or Firm*—Sprung, Horn, Kramer & Woods

[57] ABSTRACT

A process for the preparation of a supported catalyst containing a catalytically active metal such as a noble metal is disclosed wherein the supported catalyst is prepared by initially contacting the inert support with a base and disposing an amount of base in the support corresponding to 0.01 to 50 gram equivalents of base per gram equivalent of catalytically active metal to be deposited thereon, drying the so-treated support to a residual moisture content of less than 10 percent of the maximum absorbency of the support and thereafter impregnating the same with a salt solution of a catalytically active metal, e.g., a salt of a catalytically active noble metal. The inert support is one having a BET surface area of less than 20 square meters per gram. The catalyst is useful in hydrogenation, dehydrogenation, hydrogenolysis, oxidation, polymerization, isomerization or cyclization reactions.

27 Claims, No Drawings

SUPPORTED CATALYSTS AND PROCESS FOR THEIR PREPARATION

This is a continuation of application Ser. No. 066,976, filed Aug. 16, 1979.

BACKGROUND OF INVENTION

1. Field of Invention

The present invention relates to novel, highly active supported catalysts and a process for their preparation by pretreatment of an inert support material with a base and drying the so treated material to a specific residual moisture content prior to applying the catalytically active component, and to the use of the supported catalyst.

2. Discussion of Prior Art

Supported catalysts are understood as meaning compositions which contain one or more metals, as such or in the form of their compounds, in a very finely divided form on generally pre-shaped support materials and are employed for catalytic purposes. Catalysts of this type are commonly known and commercially available under very diverse designations, the active substances, in particular the noble metals, being applied in a very finely divided form, either as the metal or as a salt, to supports such as silicon dioxide, aluminium oxide, magnesium silicates and aluminium silicates, carbonates and others. Some specific examples of supported catalysts are Pd/$\alpha$-Al$_2$O$_3$ extrudates, Pd/V$_2$O$_5$/LiAl spinel spheres and platinum, palladium, rhodium, ruthenium or silver on aluminium silicate. Catalysts which have achieved very particular importance are those which contain the noble metals on supports with a small BET surface area, for example <50 m$^2$/g. They are obtained by impregnating the corresponding support material with an aqueous solution of metal salts and/or noble metal salts and by subsequent reduction. The catalysts prepared in this way contain an irregular distribution of the active substance over the support. They are used in very diverse catalytic processes, for example in oxidation, polymerization, hydrogenation, dehydrogenation, epoxidation or vinylation or in hydrocracking. In the preparation of such catalysts a number of measures are required, which can be decisive for the subsequent industrial use of the catalysts, for example when the aim is to prevent the formation of undesired by-products. For example, the influence of the surface of the support material as a cause of the formation of by-products must be taken into account. Furthermore, it can arise that active substances present within a grain of the support, that is to say are present in the centre of the grain, either do not take part at all in the reaction to be catalyzed or participate in this reaction only to a minor extent.

For many catalytic processes, such as, for example, hydrogenation reactions, Al spinels, especially alkali metal aluminum or alkaline earth metal aluminum spinels, are used. When such alkali metal aluminum or alkaline earth metal aluminum spinels are prepared, differing residual amounts of water-soluble alkali or alkaline earth remain dispersed in the grain of the support, due to the process. Due to this inhomogeneity of the spinel, a variable deposition of the active substance in the individual grains of the support necessarily results. As a consequence of this, undesired differences in activity, selectivity and catalyst life can arise when these aluminum spinel catalysts are used industrially.

The active substances enriched within a grain of the support are in general lost for the reaction to be catalyzed. In the case of costly active substances, for example from the range of noble metal compounds, this circumstance results in a financial burden on the catalyst costs per unit of product prepared.

Attempts have repeatedly been made to prepare catalysts in which support materials with a small BET surface area contain the active substances only in a narrow, outer region of the grain of the support. Amongst the many attempts which have been made, the following measures for the preparation of supported catalysts on supports with a small BET surface area have, for example, been proposed:

Impregnation of the $\alpha$-Al$_2$O$_3$ support material with an aqueous solution of a base, partial drying of the support material treated in this way to a residual moisture content of 10 to 90% of the saturation amount and subsequent spraycoating with a solution containing a metal salt German (BRD) Offenlegungsschrift No. 1,944,933;

Pretreatment of a $\gamma$-Al$_2$O$_3$ support material with a base in order to precipitate metal compounds (for example Fe(OH)$_3$) on the surface of the support, the calcining process to convert $\gamma$-Al$_2$O$_3$ to $\alpha$-Al$_2$O$_3$ with an increase in the grain size and an increase in the pore size, promoted by the precipitated Fe(OH)$_3$, and subsequent impregnation with a solution of a noble metal salt according to German (BRD) Offenlegungsschrift No. 2,517,313;

Spraying of support materials with smooth surfaces, such as, for example, of carbonates, carbides and the like, with a colloidal PdO.H$_2$O solution prepared by neutralising a PdCl$_2$—HCl solution with NaOH, ripening over a period of up to 4 days and finally carrying out a further treatment with NaOH (U.S. Pat. No. 3,271,327);

Impregnation of a Al$_2$O$_3$ support, which can contain up to 0.5% by weight of an alkali metal oxide and up to 10% by weight of a metal oxide in the form of Al spinel and is prepared by calcining Al$_2$O$_3$ of the pseudoboehmite type, with a solution of a noble metal salt, the acidity of which is in a predefined ratio to the alkali metal content of the support German (BRD)Offenlegungsschrift No. 2,715,094;

Spraying of a calcined Al$_2$O$_3$ with a concentrated, acidified solution of a Pd salt and subsequent calcining (U.S. Pat. No. 2,946,829);

Impregnation of supports which contain OH groups with a solution of noble metal-amine complex ions, which are obtained from the corresponding noble metal salts by the addition of aqueous NH$_4$OH, the support optionally being rendered hydrophobic beforehand German (BRD Offenlegungsschrift No. 2,317,536.

However, all of these processes and the catalysts thus obtainable have considerable disadvantages. In particular, these catalysts have a very high concentration of noble metal even on the surface of the support. Furthermore, differences exist between the individual catalyst particles in respect of the distribution of noble metal. A further disadvantage of the processes proposed for the preparation of the catalysts is that the support materials employed in general still have relatively large surface areas, as a result of which secondary reactions with the products can again be initiated. Furthermore, in many cases these catalysts have inadequate catalyst lives.

However, in the modern chemical industry there is a considerable demand for ever increasing amounts of supported catalysts, which, for reasons of cost, should contain as little noble metal as possible, enriched in a narrow annular zone, and should be distinguished by high selectivities and long catalyst lives.

SUMMARY OF INVENTION

A process for the preparation of supported catalysts by the treatment of inert support material with a base, subsequent drying, application of a metal salt solution and/or noble metal salt solution and, optionally, reduction of the salt to the metal has now been found, wherein an inert support material with a BET surface area of less than 20 m$^2$/g is impregnated, in accordance with the absorbency of the support material, to saturation with a base, then dried to a residual moisture content of less than 10% of the maximum absorbency of the support and impregnated in a manner which is in itself known with a metal salt solution and/or noble metal salt solution, again to saturation, and the metal salt is then optionally reduced to the metal, the base being applied, before the impregnation with the metal salt solution and/or noble metal salt solution, in an amount such that the support contains 0.01 to 50 gram equivalents of base per gram equivalent of metal to be applied.

The invention also relates to the supported catalysts per se.

Materials used as the support materials which are pretreated with bases by the process according to the invention are very diverse systems, from which the inert support material with a BET surface area of less than 20 m$^2$/g and preferably less than 10 m$^2$/g has been built up. These materials are essentially metal oxides, silicates, spinels, carbides, carbonates and the like, and mixtures thereof. Inert support materials are particularly preferred, such as, for example, aluminum oxides, silicon dioxides, silicon dioxide/aluminum oxide mixtures, amorphous silicas, kieselguhrs, barium, strontium or calcium carbonates, mixtures thereof, optionally with the addition of silicon dioxides or aluminium oxides, titanium oxides, zirconium oxides, magnesium oxides, magnesium silicates, zirconium silicates, magnesium aluminium spinel, silicon carbides, tungsten carbides, mixtures of silicon carbides with silicon dioxides or any desired mixtures thereof. The inert supports can be used in very diverse forms, such as, for example, in the form of spheres, granules, extrudates, tablets, saddles, tube sections, fragments, honeycomb ceramics and the like.

The treatment of the inert support material with a base is generally carried out at temperatures of about 5° to about 100° C., preferably at 10° to 60° C. and particularly preferentially at 20° to 40° C. The treatment can be carried out at normal pressure, under elevated pressures or under reduced pressure. The ratio of base to metal is in general 0.01 to 50, preferably 0.5 to 20 and particularly preferentially 0.5 to 10 gram equivalents of base per gram equivalent of metal. The period of action of the base, which is mixed with the support in the form of an aqueous solution or of a non-aqueous solution, is variable within wide ranges and is from 5 minutes to 72 hours.

The bases can be brought to act in very diverse forms on the inert support materials. They can be employed either solvent-free in the liquid form or in the form of solutions in aqueous or non-aqueous solvents.

It can sometimes be appropriate for the solvent used to form a homogeneous phase with the base, but this is in no way necessary for carrying out the process according to the invention. Solvents which can be used for the bases are, for example: water, straight-chain or branched hydrocarbons with 1 to 12 and preferably with 1 to 6 C atoms which contain a hydroxyl group, keto group and/or carboxyl group, cyclic hydrocarbons with 5 to 7 and preferably 6 carbon atoms in the ring system which contains a hydroxyl group, keto group and/or carboxyl group and heterocyclic compounds with preferably 6 atoms in the ring system which contain a hydroxyl group, keto group and/or carboxyl group and contain oxygen and/or nitrogen as hetero-atoms.

Particularly preferred solvents are water, alcohols, such as methanol, ethanol, propanol, isopropanol, butanol, ethylene glycol and glycerol, and also ketones, such as acetone, and mixtures thereof, hydrochloric acid, sulphuric acid, nitric acid, hydriodic acid, hydrobromic acid, acetic acid and formic acid.

Substances suitable as bases with which the inert supports are treated by the process according to the invention are compounds of very diverse types which are to be designated as bases according to the generally known theories of Brönsted or of Lewis (see textbooks on inorganic chemistry). According to these theories, all substances which, on the one hand, take up H$^+$ ions and, on the other hand, possess free electron pairs are to be designated as bases. Examples of bases which can be used are oxides, carbonates, bicarbonates, hydrogen phosphates, hydroxides, alkoxides, formates, alkali metal silicates, alkali metal aluminates or mixtures thereof.

The alkali metal silicates and alkali metal aluminates which can be used are described in Hollemann-Wiberg, "Lehrbuch der anorganischen Chemie" ("Textbook of Inorganic Chemistry", edition 71.-80., Berlin 1971, page 497, 577/578 and 583/584.

The following can be used for the pretreatment, according to the invention, of the support with bases: Li$_2$O, Na$_2$O, K$_2$O, Rb$_2$O, Cs$_2$O, MgO, LiOH, NaOH, KOH, RbOH, CsOH, Mg(OH)$_2$, Ca(OH)$_2$, Sr(OH)$_2$, Ba(OH)$_2$; Na$_2$HPO$_4$; Li$_2$HPO$_4$; K$_2$HPO$_4$; Na$_2$CO$_3$, Li$_2$CO$_3$, K$_2$CO$_3$, LiOOCCH$_3$, NaOOCCH$_3$, KOOCCH$_3$, NaHCO$_3$, LiHCO$_3$, KHCO$_3$; alkoxides of the MeOR type, where Me represents an alkali metal and R denotes a C$_1$-C$_4$-alkyl radical, such as, for example, NaOCH$_3$, NaOC$_2$H$_5$ and NaOC$_3$H$_7$, alkali metal silicates of the ME$_4{}^I$SiO$_4$, Me$_6{}^I$Si$_2$O$_7$, Me$_2{}^I$SiO$_3$ and Me$_2{}^I$Si$_2$O$_5$ type, such as, for example, Na$_2$SiO$_3$, and alkali metal aluminates, such as, for example, Na[Al(OH)$_4$].

The bases can be metered into the initially introduced supports, or vice versa. Preferably, the solution of the bases is metered into the initially introduced support.

An essential feature of the pretreatment of the inert support materials with bases is the subsequent drying in a manner which is in itself known, for example discontinuously or continuously in a drying cabinet or a stream of warm air at temperatures of about 50° to 200° C. and preferably at 100° to 150° C. Temperatures of 105° to 125° C. and pressures of 1 bar are particularly preferred. The support material loaded with alkali is dried in this way to a residual moisture content of less than 10%, preferably less than 5%, particularly preferentially less than 2% and very particularly preferentially less than 1% of the absorbency of the support.

In a subsequent process stage, the support material treated in this way is impregnated, in accordance with its absorbency, to saturation in a manner which is in itself known with a metal salt solution and/or noble metal salt solution. The metal contents and/or noble metal contents of the solutions employed in this way are calculated so that the desired metal concentrations on the support materials are obtained either by a single impregnation or by multiple impregnation. These contents also determine the requisite amounts of base, which are employed for pretreatment of the support. For example, the salt solutions of metals of groups IIIb, IVa, IVb, Va, Vb, VIa, VIIIa, Ib and IIb of the periodic table according to Mendeleev and also of the rare earths and of the actinides are used.

The following metals may be mentioned individually by way of example: Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Ga, Tl, Ge, Sn, Pb, As, Sb, Bi, Ce, Sm, Th and U. Pd, Ti, Cr, Mn, Fe, Ru, Co, Rh, Ni, Cu, Zn, Ag, Bi, Zr, Ir, Pt, Au and Ce are preferably employed.

The metals used can be employed in the form of their salts or complex salts, either as a solution or as a suspension.

Examples of salts and/or complexes of these metals which can be used are halides, for example fluorides, chlorides, bromides and iodides, such as are listed in "Halides of the Transition Elements", Volumes 1 to 3, by D. Brown, J. H. Canterford and R. Coltan, John Wiley & Sons, Ltd. London 1968, and also the types of compounds listed in "Structural Inorganic Chemistry" by A. F. Wells, 3rd edition, Oxford at the Clarendon Press 1967.

The following metal salts and noble metal salts may be mentioned preferentially: $PbCl_2$, $Pb(NO_3)_2$, $Pb(CH_3COO)_2.aq$; $CdCl_2.H_2O$, $CdI_2$, $Cd(NO_3)_2.4H_2O$, $3CdSO_4.8H_2O$, $CeCl_3.7H_2O$, $Ce(NO_3)_3.6H_2O$, $Ce(SO_4)_2.4H_2O$, $Cr(NO_3)_3.9H_2O$, $FeCl_2.4H_2O$, $FeCl_3.6H_2O$, $FeCl_3$, $Fe(NO_3)_3.9H_2O$, $FeSO_4.7H_2O$, $Fe_2(SO_4)_3.aq$, $CuBr_2$, $CuCl_2.2H_2O$, $Cu(NO_3)_2.3H_2O$, $CuSO_4.5H_2O$, $LaCl_3.7H_2O$, $La(NO_3)_3.6H_2O$, $MnCl_2.4H_2O$, $Mn(NO_3)_2.4H_2O$, $MnSO_4.H_2O$, $NiCl_2.6H_2O$, $Ni(NO_3)_2.6H_2O$, $NiSO_4.7H_2O$, $ThCl_4$, $Th(NO_3)_4.4H_2O$, $TiCl_3$, $TiCl_4$, $TiOSO_4$, $UO_2(NO_3)_2.6H_2O$, $VOSO_4.5H_2O$, $VO(C_2O_4).aq$; $Bi(NO_3)_3.5H_2O$, $Bi(NO_3).BiO(OH)$, $ZnCl_2$, $Zn(NO_3)_2.6H_2O$, $ZnSO_4.7H_2O$, $ZrOCl_2.8H_2O$, $H_2[PtCl_6]$, $K_2[PtCl_6]$, $Na_2[PdCl_4]$, $PdCl_2$, $PdBr_2$, $PdI_2$, $K_2[PdCl_6]$, $Pd(CH_3COO)_2$, $Pd(NO_3)_2$, $PdSO_4$, $[Pd(NH_3)_2]Cl_2$, $RhCl_3$, $Rh(NO_3)_3$, $H_2[IrCl_6]$, $IrCl_3$, $RuCl_3$, $AgNO_3$, $BiCl_3$, $CrCl_3$, $SmCl_3$ and $NbOCl_3$.

The chemical compositions of the metal salt solutions and/or noble metal salt solutions used is determined by the nature of the catalyst to be prepared. The solutions can contain one or more metals, dissolved in the form of their salts. Physical parameters, such as, for example, the absorbency of the support and the solubility of the metal salts and/or noble metal salts, can make it necessary to carry out repeated impregnations in the sense of the process according to the invention in order to obtain the required concentration of active substance in the finished catalyst. For example, the concentration of the metal salt solution and/or noble metal salt solution is so adjusted that the finished catalyst contains 0.5 to 200 g and preferably 1 to 100 g of one or more catalytically active components per liter of support. If the catalytically active component is a noble metal or a noble metal compound, or if the supported catalyst contains several catalytic components, at least one of which is a noble metal or a noble metal compound, the content of these components is in each case 0.5–100 g, preferably 1–50 g and particularly preferentially 2–20 g, calculated as the noble metal in the form of the element, per liter of support. For example, the catalyst according to the invention can contain, per liter of support, 1–20 g and preferably 2–10 g of palladium or 1–100 g and preferably 2–50 g of silver or, in the case of a multi-component supported catalyst, 1–20 g of palladium, 1–50 g of copper and 1–50 g of chromium, in each case calculated as the metal in the form of the element.

The possibility of carrying out the process according to the invention industrially is illustrated with the aid of the preparation of a palladium-containing $\alpha$-$Al_2O_3$ catalyst.

The $\alpha$-$Al_2O_3$ is pretreated, in accordance with its absorbency, with a solution of a base, for example NaOH in $H_2O$, in a ratio of 0.01 to 50 equivalents of base per equivalent to be added, prior to the actual impregnation with the solution of the metal salt. The support material is then dried at a temperature of 100° to 200° C., for example 110° C., to a residual moisture content of <10%, for example <1%, of the absorbency of the support. The support material pretreated in this way is impregnated, in accordance with its absorbency (by processes which are in themselves known) with a solution of a metal salt, for example $Na_2[PdCl_4]$, the metal content of the solution being determined by the amount of base previously applied. After a reaction time of from a few hours to several days, for example 24 hours, a washing process and drying follow. If necessary, the metal salt applied is first reduced to the metal by known methods, for example by treatment with $N_2H_4.H_2O$ solution, before a washing process and drying follow.

An essential advantage of the process according to the invention over the processes previously known for the preparation of supported catalysts is that an annular enrichment of the active substances within the inert support material, that is to say directly below the surface, is achieved, by which means distinct savings are achieved, especially in the case of the expensive noble metals. When used industrially, the catalysts obtained in this way produce fewer by-products than supported catalysts of the conventional type, because of the small surface area of the support material. Furthermore, the active substances enriched in the support are substantially protected against poisoning and losses due to abrasion. As a result of this, a very long catalyst life with constant activity is obtained.

The supported catalysts prepared according to the invention can be used for very diverse catalytic processes, such as, for example, hydrogenation, dehydrogenation, hydrogenolysis, oxidation, polymerization, isomerisation or cyclisation. In these catalytic reactions, the supported catalysts prepared by the process according to the invention can be employed either in the sump phase or in the trickle phase and the gas phase. The trickle phase and the gas phase are preferred. The reactions can be carried out either under normal pressure or excess pressure or under reduced pressure. Catalytic hydrogenation reactions are a preferred field of application for the catalysts prepared according to the invention. Depending on the composition of the active substance, the catalysts are particularly suitable for the hydrogenation of aliphatic multiple bonds, for example for selective hydrogenation reactions, for the hydrogenation of aromatic systems in the nucleus or for the hydrogenation of specific substituents, for example of nitro or carbonyl groups contained in aromatic systems. Specific compositions of active substance in the supported catalysts prepared by the process according to the invention have found a preferred application in the catalytic hydrogenation of substituted aromatic compounds and in this case—depending on the combination of catalytically active substances and on other process parameters, such as temperature or pressure—either the aromatic system and/or the substituent can be hydrogenated.

Thus, for example, the active substance combination of palladium/vanadium/lead on inert α-$Al_2O_3$ support, which has been treated by the process according to the invention, finds preferred application in the catalytic hydrogenation of nitro-aromatic compounds, such as, for example, of nitrobenzene, nitrotoluene, dinitrobenzenes, dinitrotoluenes, trinitrotoluenes and nitrophenols to the corresponding aromatic amines. For mononitro compounds the gas phase reaction is preferred, whilst for the dinitro or trinitro compounds the liquid phase and especially the trickle phase is preferred. Both in the gas phase and in the trickle phase, the compound to be reduced is generally passed over a fixed catalyst. The reaction is advantageously carried out with an excess of hydrogen. When the reaction is carried out in the trickle phase, the nitro compound to be reduced is usually diluted with the amino compound formed during the reduction or with another diluent to an extent such that there is no danger in carrying out the reduction. The preferred reaction temperature in the trickle phase is in the range of 50° to 150° C. and the preferred pressure range is between 1 and 100 bars.

In the case of hydrogenation in the gas phase, the reaction is preferably carried out in a temperature range of 150° to 350° C. and under 1 to 10 bars.

A catalyst prepared by the process according to the invention by the deposition of palladium on inert α-$Al_2O_3$ finds, in turn, particular application in the hydrogenation of phenol or of m/p-cresol to cyclohexanone or, respectively, m/p-methylcyclohexanone. In this case the hydrogenation is advantageously carried out in the gas phase. The preferred temperature range is from 100° to 200° C. The reaction is usually carried out under normal pressure or under a slight excess pressure of 0.1 to 1 bar.

The catalytic reactions carried out with supported catalysts prepared according to the invention are distinguished by high selectivity and low by-product formation. The constant catalyst activity gives rise to long operating times.

EXAMPLES (A) Description of the support materials emloyed

TABLE 1

| Support No. | Support composition | Geometric form | BET $m^2/g$ | Bulk density g/l | Absorption of $H_2O$ ml/100 g |
|---|---|---|---|---|---|
| 1 | $Al_2O_3$ <5% $SiO_2$ | extrudate 3 mm φ | 3.1 | 1,161 | 28.0 |
| 2 | $Al_2O_3$ <5% $SiO_2$ | extrudate 5 mm φ | 6.0 | 1,075 | 26.4 |
| 3 | $Al_2O_3$ <5% $SiO_2$ | extrudate 2 mm φ | 9.0 | 962 | 32.0 |
| 4 | $Al_2O_3$ | spheres 3–6 mm | 9.8 | 812 | 45.1 |
| 5 | $Al_2O_3$ | tablets 5 × 5 mm | 8.5 | 562 | 85.0 |
| 6 | $Al_2O_3$ ~5% $Li_2O$ | spheres 4–5.5 mm | 20.0 | 770 | 44.0 |
| 7 | Al silicate ~88% $SiO_2$ ~12% $Al_2O_3$ | granules 3.5–4.5 mm | 1.8 | 760 | 32.3 |
| 8 | Al silicate ~85% $Al_2O_3$ ~15% $SiO_2$ | granules 3–5 mm φ | 4.5 | 1,190 | 22.4 |
| 9 | Al silicate ~85% $Al_2O_3$ >10% $SiO_2$ | spheres 4–5 mm φ | 0.1 | 932 | 12.6 |
| 10 | Mg Al silicate ~53% $Al_2O_3$ ~32% $SiO_2$ ~15% MgO | spheres 6 mm φ | 2.1 | 1,060 | 21.0 |
| 11 | Al silicate ~88% $SiO_2$ ~12% $Al_2O_3$ | spheres 8 mm φ | 1.0 | 1,000 | 28.6 |
| 12 | Zr Mg silicate ~88% $SiO_2$ ~6% $ZrO_2$ ~3% MgO remainder $Al_2O_3$ | spheres 8 mm φ | 5.6 | 1,050 | 12.4 |
| 13 | $SiO_2$ <5% $Al_2O_3$ | spheres 5 mm φ | 10.0 | 834 | 27.0 |
| 14 | $SiO_2$ | tablets 3 × 3 mm | 6.5 | 1,132 | 11.0 |
| 15 | Al silicate ~85% $SiO_2$ ~15% $Al_2O_3$ | tablets 4 × 4 mm | 3.9 | 1,198 | 9.0 |

(B) Preparation of the catalysts

Example 1

(a) General description of the preparation of the catalyst 1,000 ml of a support from Table 1 are impregnated to saturation at room temperature, in a rotating drum, with a solution containing the requisite amount of base.

The volume of the impregnating solution is calculated via the absorbency and the bulk density of the support.

The impregnating solution accordingly employed is completely absorbed by the particular support within a few minutes. The support impregnated in this way is dried to constant weight, in a rotating drum or in another suitable vessel, in a warm stream of optionally inert gas at up to 200° C.

After cooling to room temperature, the residual moisture content of the dried, base-impregnated support must be within a range of less than 10% of the saturation amount of the support. The dry support pretreated in this way is again impregnated in accordance with its absorbency with a solution containing the requisite amount of active substance, as described above. After this impregnation, the moist support is filled into a suitable, closable vessel and left in this vessel for up to several days, corresponding to a ripening period. The support treated in this way is then washed with water and/or dried.

If necessary, the active substances deposited on the support are reduced by generally known methods and the catalyst is then washed with water and optionally dried.

(b) Individual example

For example, 1,000 ml of support No. 1 from Table 1, corresponding to 1,161 g with an absorbency of 28 ml of water per 100 g of support, are impregnated with 1.2 g=0.03 g equivalent of sodium hydroxide solution, dissolved in 325 ml of water. The impregnating solution is completely absorbed by the support within 2 minutes. The moist support is transferred to a cylindrical vessel of appropriate size and dried in a stream of warm air at 110° C. to constant weight and to a residual moisture content of 0.11% by weight, corresponding to about 0.39% of the saturation amount.

The support pretreated in this way is then again impregnated with an aqueous solution, containing 2.0 g=0.037 g equivalent, of palladium in the form of sodium tetrachloropalladate-II, the volume of this solution corresponding to the absorbency of the support to saturation, and transferred moist into a closable vessel of appropriate size.

The amount of NaOH contained in the support corresponds to an equivalent ratio [g equivalent of NaOH:g equivalent of Pd] of 0.81. After a reaction time of 15 minutes, support No. 1, which has been impregnated with sodium tetrachloropalladate-II and pretreated with sodium hydroxide solution, is covered, in the storage vessel, with a layer of 400 ml of an aqueous solution containing 10% of hydrazine hydrate, by which means the palladium compound deposited on the support is reduced to metallic palladium. After a reaction time of 2 hours, the reduction solution is decanted off. The catalyst is washed with water until no further reducing agent and no further ions of the compounds used in the preparation of the catalyst are detectable in the wash water. Drying of the catalyst is carried out as described above, in a stream of warm air at 110° C. The catalyst prepared in this way contains 2 g of palladium per liter of support (approximately 0.172% by weight) in an annular zone located inside and just below the surface of the support.

The catalysts prepared by the process according to the invention were tested as follows to determine their catalytic characteristics:

(c) Testing in the liquid phase in a laboratory hydrogenation apparatus

Testing to determine the catalytic activity of catalysts is carried out by a standardised method for the hydrogenation of o-nitrotoluene in methanolic solution in a laboratory hydrogenation apparatus. The apparatus used for this purpose corresponds, in its essential construction, to shaking or stirred apparatuses of the designs known from the literature, such as are described, for example, in "Methoden der organischen Chemie" ("Methods of Organic Chemistry") (Houben-Weyl) Volume IV/2, Georg Thieme Verlag, Stuttgart, 1955 and in the Fachzeitschrift für das Laboratorium, G-I-T Verlag, Darmstadt, in the September 1965 and October 1974 issues.

For the test, 10 ml of catalyst are employed for the hydrogenation of 5 g of o-nitrotoluene (Merck, 98% purity) in 50 ml of methanol (Merck, 99% purity) at a constant hydrogenation temperature of 50° C. and under a constant pressure of 1,000 mm water gauge. The hydrogenation is carried out in a glass vessel with a useful capacity of 100 ml by a vertical shaking motion of constant stroke (205 strokes/minute), height of stroke 80 mm). The rate at which hydrogen is taken up is taken as a measure of the hydrogenation activity of the particular catalyst employed and, by means of automatic, graphical plotting, shows the course of the hydrogenation with time. The hydrogenation results obtainable under identical conditions and in the same apparatus have very good reproducibility and can be used to assess the catalytic activity of the catalysts employed relative to one another.

However, they are not absolute values, since when a catalyst is tested in a laboratory hydrogenation apparatus, the apparatus-specific factor of the hydrogenation apparatus used must be taken into account. Therefore, when a catalyst is tested in a different hydrogenation apparatus, such as, for example, in the system Roche-Kühner Type NDH low-pressure hydrogenation apparatus described in the G-I-T Fachzeitschrift für das Laboratorium, No. 10, October 1974, pages 974 to 976, G-I-T Verlag Ernst Giebeler, Darmstadt, it is entirely possible to obtain different hydrogenation results, but the differences in activity to be expected fall within the same gradings.

The result of the activity test on the catalyst prepared according to Example 1 is given in Table 7. It can be seen that the hydrogenation had ended after a hydrogenation period of 54 minutes and that, after this time, 100% of the o-nitrotoluene employed had been converted.

Examples 2 to 21

Use of inert $Al_2O_3$ supports No. 1 to 5 from Table 1

In accordance with Example 1(a), $Al_2O_3$ supports were subjected to a pretreatment with NaOH, with subsequent loading with palladium according to Table 2:

TABLE 2

| Example No. | Pretreatment of, in each case, 1,000 ml of support with aqueous NaOH solution | | | | Residual moisture content after drying % of saturation | Loading of the treated support with palladium in the form of aqueous $Na_2(PdCl_4)$ solution | | g equivalent of NaOH per g equivalent of palladium |
|---|---|---|---|---|---|---|---|---|
| | Support employed No. | NaOH employed | | | | Palladium employed | | |
| | | g | g equivalent | ml of solution | | g | g equivalent | |
| 2 | 1 | 1,161 | 1.8 | 0.045 | 325 | 0.4 | 3 | 0.056 | 0.80 |
| 3 | 1 | 1,161 | 6.0 | 0.150 | 325 | 0.9 | 3 | 0.056 | 2.68 |
| 4 | 2 | 1,075 | 0.2 | 0.005 | 284 | 0.3 | 2 | 0.037 | 0.14 |
| 5 | 2 | 1,075 | 0.4 | 0.010 | 284 | 0.6 | 2 | 0.037 | 0.27 |
| 6 | 2 | 1,075 | 0.8 | 0.020 | 284 | 0.4 | 2 | 0.037 | 0.54 |

TABLE 2-continued

| Example No. | Pretreatment of, in each case, 1,000 ml of support with aqueous NaOH solution | | | | Residual moisture content after drying % of saturation | Loading of the treated support with palladium in the form of aqueous Na₂(PdCl₄) solution | | g equivalent of NaOH per g equivalent of palladium |
|---|---|---|---|---|---|---|---|---|
| | Support employed | | NaOH employed | | | Palladium employed | | |
| | No. | g | g | g equivalent | ml of solution | | g | g equivalent | |
| 7 | 2 | 1,075 | 1.2 | 0.030 | 284 | 0.3 | 2 | 0.037 | 0.81 |
| 8 | 2 | 1,075 | 1.6 | 0.040 | 284 | 0.5 | 2 | 0.037 | 1.08 |
| 9 | 2 | 1,075 | 2.0 | 0.050 | 284 | 0.7 | 2 | 0.037 | 1.35 |
| 10 | 2 | 1,075 | 2.4 | 0.060 | 284 | 0.6 | 2 | 0.037 | 1.62 |
| 11 | 2 | 1,075 | 4.0 | 0.100 | 284 | 0.7 | 2 | 0.037 | 2.70 |
| 12 | 3 | 962 | 1.2 | 0.030 | 308 | 0.3 | 2 | 0.037 | 0.81 |
| 13 | 4 | 812 | 1.2 | 0.030 | 366 | 0.2 | 2 | 0.037 | 0.81 |
| 14 | 4 | 812 | 3.0 | 0.075 | 366 | 0.3 | 2 | 0.037 | 2.03 |
| 15 | 4 | 812 | 7.5 | 0.188 | 366 | 0.7 | 2 | 0.037 | 5.08 |
| 16 | 4 | 812 | 3.0 | 0.075 | 366 | 0.3 | 5 | 0.094 | 0.80 |
| 17 | 4 | 812 | 7.5 | 0.188 | 366 | 0.7 | 5 | 0.094 | 2.00 |
| 18 | 4 | 812 | 10.8 | 0.270 | 366 | 0.9 | 9 | 0.169 | 1.60 |
| 19 | 4 | 812 | 43.2 | 1.080 | 366 | 1.3 | 9 | 0.169 | 6.39 |
| 20 | 4 | 812 | 86.4 | 2.160 | 366 | 2.1 | 9 | 0.169 | 12.78 |
| 21 | 5 | 562 | 6.0 | 0.150 | 478 | 0.2 | 5 | 0.094 | 1.60 |

The supports loaded with palladium in this way in each case contain the palladium in the same distribution within a narrow zone inside, and just below the surface of, the support.

Examples 22 to 29

Comparison examples without pretreatment of supports No. 1 to 4 from Table 1 with NaOH Analogously to Example 1(a), but without pretreatment of the support with NaOH, in each case 1,000 ml of support were impregnated, in accordance with Table 3, with an aqueous solution containing sodium tetrachloropalladate-II, the volume of solution corresponding to the absorbency of the support to saturation, and then, after a reaction time of 15 minutes, reduced with hydrazine hydrate, washed with water and dried.

TABLE 3

| Example No. | Support employed | | Loading of the support with palladium in the form of aqueous Na₂[PdCl₄] solution | | |
|---|---|---|---|---|---|
| | No. | g | g of Pd | g equivalent of Pd | ml of solution |
| 22 | 1 | 1,161 | 2 | 0.037 | 325 |
| 23 | 1 | 1,161 | 3 | 0.056 | 325 |
| 24 | 2 | 1,075 | 2 | 0.037 | 284 |
| 25 | 2 | 1,075 | 5 | 0.094 | 284 |
| 26 | 3 | 962 | 2 | 0.037 | 308 |
| 27 | 4 | 812 | 2 | 0.037 | 366 |
| 28 | 4 | 812 | 5 | 0.094 | 366 |
| 29 | 4 | 812 | 9 | 0.169 | 366 |

The supports loaded with palladium in this way without pretreatment with NaOH in each case contain the palladium in an inhomogeneous form and in some cases distributed throughout the entire grain of the support.

Example 30

Comparison example according to the prior art on support No. 6 from Table 1

If a spinel support described in German (BRD) Offenlegungsschrift No. 2,135,155, which corresponds to support No. 6 from Table 1, is used as the starting material, in order to load this support with palladium, no pretreatment with NaOH is carried out because of the alkalinity of the support. This is because of the spinel support contains water-soluble Li₂O, which, due to the process, is dispersed in varying amounts in the individual grains of the support.

On impregnating 1,000 ml of support No. 6 with 9 g of Pd in the form of Na₂[PdCl₄] dissolved in 339 ml of water, and subsequently reducing the salt with aqueous hydrazine hydrate solution and washing and drying the product, a catalyst is obtained in which the palladium distribution in the individual spheres of catalyst exhibits all gradations between annular deposition of palladium on the surface of the catalyst to complete penetration to the inside of the sphere.

Examples 31 to 39

Use of other inert supports 7 to 15 from Table 1

Analogously to Example 1(a), supports No. 7 to 15 were subjected to a pretreatment with NaOH, with subsequent loading with palladium, in accordance with Table 4:

TABLE 4

| Example No. | Pretreatment of, in each case, 1,000 ml of support with aqueous NaOH solution | | | | Residual moisture content after drying % of saturation | Loading of the treated support with palladium in the form of aqueous Na₂(PdCl₄) solution | | g equivalent of NaOH per g equivalent of palladium |
|---|---|---|---|---|---|---|---|---|
| | Support employed | | NaOH employed | | | Palladium employed | | |
| | No. | g | g | g equivalent | ml of solution | | g | g equivalent | |
| 31 | 7 | 760 | 3.0 | 0.075 | 245 | 0.4 | 5 | 0.094 | 0.80 |
| 32 | 8 | 1,190 | 3.0 | 0.075 | 267 | 0.6 | 5 | 0.094 | 0.80 |
| 33 | 9 | 932 | 6.0 | 0.150 | 117 | 0.8 | 5 | 0.094 | 1.60 |
| 34 | 10 | 1,060 | 12.0 | 0.300 | 223 | 0.3 | 10 | 0.187 | 1.60 |

TABLE 4-continued

| Example No. | Support employed No. | Pretreatment of, in each case, 1,000 ml of support with aqueous NaOH solution | | | Residual moisture content after drying % of saturation | Loading of the treated support with palladium in the form of aqueous Na$_2$(PdCl$_4$) solution | | g equivalent of NaOH per g equivalent of palladium |
|---|---|---|---|---|---|---|---|---|
| | | NaOH employed | | | | Palladium employed | | |
| | | g | g equivalent | ml of solution | | g | g equivalent | |
| 35 | 11 | 1,000 | 12.0 | 0.300 | 286 | 0.4 | 10 | 0.187 | 1.60 |
| 36 | 12 | 1,050 | 6.0 | 0.150 | 130 | 0.7 | 5 | 0.094 | 1.60 |
| 37 | 13 | 834 | 7.5 | 0.188 | 225 | 0.5 | 10 | 0.187 | 1.01 |
| 38 | 14 | 1,132 | 12.0 | 0.300 | 125 | 0.8 | 10 | 0.187 | 1.60 |
| 39 | 15 | 1,198 | 7.5 | 0.188 | 108 | 0.8 | 5 | 0.094 | 2.00 |

Examples 40 to 50

Use of bases other than NaOH for pretreatment of the support, using supports from Table 1

Analogously to Example 1(a), the supports were subjected to a pretreatment with a base, with subsequent loading with palladium, in accordance with Table 5, the support in each case having been treated with a base other than NaOH before loading with palladium.

Examples 51 to 67

Pretreatment of support No. 4 from Table 1 with NaOH, with subsequent loading with active substances other than palladium and with combinations of active substances including palladium Analogously to Example 1(a), 1,000 ml=812 g of support No. 4 were emloyed for each batch and, in accordance with Table 6, impregnated with a volume of

TABLE 5

| Example No. | Support employed No. | Pretreatment of, in each case, 1,000 ml of support with an aqueous solution of a base | | | | Residual moisture content after drying % of saturation | Loading of the treated support with palladium in the form of aqueous Na$_2$(PdCl$_4$) solution | | g equivalent of base per g equivalent of palladium |
|---|---|---|---|---|---|---|---|---|---|
| | | | Base employed | | | | Palladium employed | | |
| | | g | Base | g | g equivalent | ml of solution | | g | g equivalent | |
| 40 | 1 | 1,161 | Na$_2$CO$_3$ | 3.0 | 0.057 | 325 | 0.2 | 2 | 0.037 | 1.54 |
| 41 | 2 | 1,075 | Na$_2$HPO$_4$.12H$_2$O | 13.5 | 0.075 | 284 | 0.4 | 2 | 0.037 | 2.03 |
| 42 | 2 | 1,075 | KHCO$_3$ | 3.8 | 0.038 | 284 | 0.2 | 2 | 0.037 | 1.03 |
| 43 | 2 | 1,075 | NaC$_2$H$_3$O$_2$ 3H$_2$O | 5.0 | 0.037 | 284 | 0.3 | 2 | 0.037 | 1.00 |
| 44 | 2 | 1,075 | Ba(C$_2$H$_3$O$_2$)$_2$ H$_2$O | 10.0 | 0.073 | 284 | 0.4 | 2 | 0.037 | 1.97 |
| 45 | 2 | 1,075 | Mg(C$_2$H$_3$O$_2$)$_2$ 4H$_2$O | 8.0 | 0.075 | 284 | 0.4 | 2 | 0.037 | 2.03 |
| 46 | 4 | 812 | KOH | 10.5 | 0.187 | 366 | 0.3 | 5 | 0.094 | 1.99 |
| 47 | 4 | 812 | LiOH (98%) | 4.5 | 0.184 | 366 | 0.3 | 5 | 0.094 | 1.96 |
| 48 | 4 | 812 | NaHCO$_3$ | 8.0 | 0.095 | 366 | 0.4 | 5 | 0.094 | 1.01 |
| 49 | 4 | 812 | K$_2$CO$_3$ | 13.0 | 0.188 | 366 | 0.2 | 5 | 0.094 | 2.00 |
| 50 | 4 | 812 | HCO$_2$Na | 23.0 | 0.338 | 366 | 0.3 | 9 | 0.169 | 2.00 |

366 ml of an aqueous solution containing NaOH, this volume corresponding to the absorbency of the support to saturation, dried and then subjected to loading with active substances.

TABLE 6

| Example No. | Pretreatment of 1,000 ml-812 g of support No. 4 with 366 ml of aqueous NaOH solution | | Residual moisture content after drying % of saturation | Loading of the treated support with active substances in the form of their salts in aqueous solution | | | | g equivalent of NaOH per g equivalent of total metals |
|---|---|---|---|---|---|---|---|---|
| | NaOH employed | | | Active substance employed | | | | |
| | | | | Salt | | Metal | | |
| | g | g equivalent | | g | Salt | g | g equivalent | Sum g equivalent | |
| 51 | 30 | 0.750 | 0.7 | 71.2 | FeCl$_2$.4H$_2$O | 20 | 0.716 | 0.716 | 1.05 |
| 52 | 30 | 0.750 | 0.7 | 81.0 | NiCl$_2$.6H$_2$O | 20 | 0.681 | 0.681 | 1.10 |
| 53 | 30 | 0.750 | 0.7 | 80.8 | CoCl$_2$.6H$_2$O | 20 | 0.679 | 0.679 | 1.11 |
| 54 | 30 | 0.750 | 0.7 | 45.8 | MnCl$_2$ | 20 | 0.728 | 0.728 | 1.03 |
| 55 | 26 | 0.650 | 0.6 | 24.9 | Na$_2$[PdCl$_4$] | 9 | 0.169 | 0.527 | 1.23 |
| | | | | 35.6 | FeCl$_2$.4H$_2$O | 10 | 0.358 | | |
| 56 | 26 | 0.650 | 0.6 | 24.9 | Na$_2$[PdCl$_4$] | 9 | 0.169 | 0.510 | 1.27 |
| | | | | 40.5 | NiCl$_2$.6H$_2$O | 10 | 0.341 | | |

TABLE 6-continued

| Example No. | Pretreatment of 1,000 ml-812 g of support No. 4 with 366 ml of aqueous NaOH solution NaOH employed | | Residual moisture content after drying % of saturation | Loading of the treated support with active substances in the form of their salts in aqueous solution Active substance employed | | | | g equivalent of NaOH per g equivalent of total metals |
|---|---|---|---|---|---|---|---|---|
| | | | | | | Metal | | |
| | g | g equivalent | | g | Salt | g | g equivalent | Sum g equivalent | |
| 57 | 26 | 0.650 | 0.6 | 24.9 | $Na_2[PdCl_4]$ | 9 | 0.169 | 0.509 | 1.28 |
| | | | | 40.4 | $CoCl_2.6H_2O$ | 10 | 0.340 | | |
| 58 | 26 | 0.650 | 0.6 | 24.9 | $Na_2[PdCl_4]$ | 9 | 0.169 | 0.533 | 1.22 |
| | | | | 22.9 | $MnCl_2$ | 10 | 0.364 | | |
| 59 | 45 | 1.125 | 0.9 | 24.9 | $Na_2[PdCl_4]$ | 9 | 0.169 | 0.867 | 1.30 |
| | | | | 24.2 | $CuCl_2.2H_2O$ | 9 | 0.283 | | |
| | | | | 36.9 | $CrCl_3.6H_2O$ | 7.2 | 0.415 | | |
| 60 | 80 | 2.00 | 1.9 | 24.9 | $Na_2[PdCl_4]$ | 9 | 0.169 | 1.567 | 1.28 |
| | | | | 48.3 | $CuCl_2.2H_2O$ | 18 | 0.567 | | |
| | | | | 73.8 | $CrCl_3.6H_2O$ | 14.4 | 0.831 | | |
| 61 | 11(10)$^x$ | 0.275 | 0.4 | 24.9 | $Na_2[PdCl_4]$ | 9 | 0.169 | 0.212 | 1.30 |
| | | | | 4.5 | $BiCl_3$ (dissolved in HCl) | 3 | 0.043 | | |
| 62 | 11(20)$^x$ | 0.275 | 0.4 | 24.9 | $Na_2[PdCl_4]$ | 9 | 0.169 | 0.255 | 1.08 |
| | | | | 9.0 | $BiCl_3$ (dissolved in HCl) | 6 | 0.086 | | |
| 63 | 10 | 0.250 | 0.4 | 16.6 | $Na_2[PdCl_4]$ | 6 | 0.112 | 0.158 | 1.58 |
| | | | | 6.1 | $Na[AuCl_4].2H_2O$ | 3 | 0.046 | | |
| 64 | 8 | 0.200 | 0.3 | 25.3 | $Th(NO_3)_4.6H_2O$ | 10 | 0.172 | 0.172 | 1.16 |
| 65 | 10 | 0.250 | 0.4 | 24.3 | $SmCl_3.6H_2O$ | 10 | 0.199 | 0.199 | 1.26 |
| 66 | 50 | 1.250 | 1.3 | 32.3 | $TiCl_3$ (15% strength solution) | 10 | 0.626 | 0.626 | 2.00 |
| 67 | 20 | 0.500 | 0.5 | 78.7 | $AgNO_3$ | 50 | 0.463 | 0.463 | 1.08 |

Example 68

Use of non-aqueous solutions for the pretreatment of the support with a base and for loading the pretreated support with active substances Analogously to the procedure of Example 1(a), a further catalyst was prepared, with the modification that 1,000 ml of support No. 4 from Table 1 were impregnated with 28 g=0.519 g equivalent, of sodium methylate, dissolved in 366 ml of methanol, dried and then again impregnated with 40.5 g=0.341 g equivalent, of nickel-II chloride hexahydrate, dissolved in 366 ml of methanol, and dried.

The amount of sodium methylate contained in the support corresponded to an equivalent ratio (g equivalent of $CH_3ONa$ to g equivalent of Ni) of 1.52.

The catalyst prepared in this way contains the active substance in an annular zone located inside, and just below the surface of, the support.

Example 69

Loading of a Pd-containing catalyst with further active substances 1,000 ml of the catalyst prepared according to Example 18, Table 2, which contains 9 g of palladium per liter of support, were impregnated with an aqueous solution containing 9 g of vanadium in the form of vanadyl oxalate, and dried. The active substances previously applied to the support were then subjected to a heat treatment with air. After this treatment, the catalyst thus obtained was again impregnated with an aqueous solution containing 3 g of lead in the form of lead acetate, and dried.

Example 70

Testing of the catalysts prepared according to the invention in the laboratory hydrogenation apparatus according to Example 1 (c)

TABLE 7

| Example No. | from Table No. | Support No. | Pd content g/l | g equivalent of NaOH per g equivalent of Pd | Hydrogenation time in minutes | Conversion of nitrotoluene % |
|---|---|---|---|---|---|---|
| 1 | 1 | 1 | 2 | 0.81 | 54 | 100 |
| 22 Comparison | 3 | 1 | 2 | 0.00 | 60 | 55 |
| 2 | 2 | 1 | 3 | 0.80 | 41 | 100 |
| 3 | 2 | 1 | 3 | 2.68 | 33 | 100 |
| 23 Comparison | 3 | 1 | 3 | 0.00 | 60 | 92 |
| 5 | 2 | 2 | 2 | 0.27 | 50 | 100 |
| 6 | 2 | 2 | 2 | 0.54 | 43 | 100 |
| 10 | 2 | 2 | 2 | 1.62 | 36 | 100 |
| 24 Comparison | 3 | 2 | 2 | 0.00 | 56 | 100 |
| 25 Comparison | 3 | 2 | 5 | 0.00 | 41 | 100 |
| 12 | 2 | 3 | 2 | 0.81 | 46 | 100 |
| 26 Comparison | 3 | 3 | 2 | 0.00 | 60 | 77 |

TABLE 7-continued

| Example No. | from Table No. | Support No. | Pd content g/l | g equivalent of NaOH per g equivalent of Pd | Hydrogenation time in minutes | Conversion of nitrotoluene % |
|---|---|---|---|---|---|---|
| 13 | 2 | 4 | 2 | 0.81 | 60 | 85 |
| 14 | 2 | 4 | 2 | 2.03 | 55 | 100 |
| 15 | 2 | 4 | 2 | 5.08 | 41 | 100 |
| 27 Comparison | 3 | 4 | 2 | 0.00 | 60 | 35 |
| 16 | 2 | 4 | 5 | 0.80 | 46 | 100 |
| 17 | 2 | 4 | 5 | 2.00 | 31 | 100 |
| 28 Comparison | 3 | 4 | 5 | 0.00 | 52 | 100 |
| 18 | 2 | 4 | 9 | 1.60 | 32 | 100 |
| 19 | 2 | 4 | 9 | 6.39 | 27 | 100 |
| 20 | 2 | 4 | 9 | 12.78 | 20 | 100 |
| 29 Comparison | 3 | 4 | 9 | 0.00 | 39 | 100 |

The hydrogenation results listed in Table 7 clearly show that the catalysts prepared by the process according to the invention by pretreatment of the support with a base possess a substantially higher hydrogenation activity than the comparison catalysts prepared by a conventional method without pretreatment of the support with a base. It can be clearly seen that, for example, the catalyst containing 2 g of Pd per liter of support which was prepared according to Example 15 by the process according to the invention possesses an activity which is more than 4 times greater than that of the comparison catalyst with the same Pd content prepared according to Example 27.

It can also be clearly seen that the catalyst prepared according to Example 15, according to the invention, which contains only 2 g of Pd per liter of support still possesses a better activity than the comparison catalyst prepared according to Example 28, which has a Pd content of 5 g of the Pd per liter of support. Moreover, it can be seen that this catalyst prepared by the process according to the invention and containing 2 g of Pd per liter has a hydrogenation activity which is virtually as high as that of the comparison catalyst prepared according to Example 29 which contains 9 g of Pd per liter.

Example 71

Industrial hydrogenation of o-nitrotoluene

A tube reactor (tube length 6 m; tube diameter 24 mm) was filled with 2.4 liters of the catalyst prepared according to Example 69, which contained, calculated as the metals, 9 g of Pd, 9 g of V and 3 of Pb per liter of α-Al$_2$O$_3$ support. The o-nitrotoluene (4 parts) to be hydrogenated was pumped, as a mixture with o-toluidine (6 parts) at a rate of 1 kg/hour liter of catalyst, at room temperature and under a hydrogen pressure of about 50 bars, from the top onto the catalyst, where it trickled downwards over the catalyst into a separator. The hydrogen was passed through the reactor in co-current, from top to bottom, a partial amount being let-down from the gas phase after leaving the reactor, in order to remove the inert constituents from the system. A proportion of the hydrogenated liquid phase was pumped back, as recycled material, to the top of the reactor. The outlet temperature of the reactor was 110° C. After 600 hours in operation, the catalyst still had the original activity. No further nitrotoluene was detectable in the reaction product. The product contained about 500 ppm of amine hydrogenated in the nucleus. The content of higher-boiling by-products was 350 ppm. The yield of o-toluidine was 99.7%.

Example 72

Industrial hydrogenation of phenol

Vaporized phenol was passed, in a stream of hydrogen (3,000 kg of phenol/hour; molar ratio of phenol:hydrogen = 1:6), from bottom to top through a tube reactor (tube length 6 m; tube diameter 50 mm; number of tubes 366) which was heated to an average of 140° C. with high-pressure steam and was filled with 4,200 liters of a catalyst, containing 9 g of Pd/liter of α-Al$_2$O$_3$ support, prepared according to Example 18—after prior activation with hydrogen (in general 200° C., 10 hours). The catalyst temperatures were between 140° and 190° C. After passing through the reactor, the gaseous reaction products were condensed. A partial amount of the circulated hydrogen was withdrawn from the system, in order to remove inert gas constituents.

The resulting reaction product consisted of 96.2% of cyclohexanone and 3.7% of cyclohexanol. The phenol content was less than 0.05%. Based on 1 liter of catalyst, 5,300 kg of cyclohexanone were produced.

What is claimed is:

1. A supported catalyst comprising an inert support material having a BET surface area of less than 20 square meters per gram and a catalytically active material disposed in an annular zone located inside and just below the surface of said inert support prepared by a process consisting essentially of:
   A. contacting said inert support, prior to any impregnation with the catalytically active metal in accordance with its absorbency to saturation, with a solution of a base so as to dispose within said inert support 0.01 to 50 grams equivalents of base per gram equivalent of catalytically active metal to be impregnated within said inert support;
   B. drying the so-base-treated inert support at a temperature of 50° to 200° C. so that said inert support has a constant weight and has a residual moisture content of less than 10 percent of the maximum obsorbency of the support; and
   C. impregnating the so-dried inert material in accordance with its absorbency to saturation with a solution of a catalytically active metal; and
   D. washing, drying and reducing or calcining the so-impregnated inert material.

2. A catalyst according to claim 1 wherein said supported catalyst comprises a noble metal in compound or elemental form and said solution of a metal salt is a solution of a noble metal salt.

3. A process for preparing a supported catalyst according to claim 1, which consists essentially of the steps of:
   A. contacting an inert support material having a BET surface area of less than 20 square meters per gram with a base such as to dispose within said inert support material 0.01 to 50 gram equivalents of base per gram equivalent of metal to be inserted pursuant to step C;
   B. drying the so-base-treated inert support at a temperature of 50°–200° C. so that said inert support has a constant weight and a residual moisture content of less than 10 percent of the maximum absorbency of the support;
   C. impregnating the so-dried inert support material with a salt solution of a catalytically active metal; and
   D. washing, drying, and reducing or calcining the so-impregnated inert material whereby the catalytically active metal is disposed in an annular zone located inside and just below the surface of said inert support.

4. A supported catalyst according to claim 1 wherein said catalytically active metal is present on or in said support in elemental or compound form.

5. A process according to claim 3 wherein following impregnation of said support material with said solution of said catalytically active metal the metal on or in said support is reduced.

6. A process according to claim 3 wherein said inert support is a metal oxide, silicate, spinel, carbide, or carbonate or a mixture thereof.

7. A process according to claim 3 wherein the amount of base added to said inert support is 0.5 to 20 gram equivalents per gram equivalent of metal applied in accordance with step C and said base is added in the form of an aqueous solution.

8. A process according to claim 3 wherein step B is carried out until the residual moisture content of the support is less than 2 percent of its maximum absorbency.

9. A process according to claim 3 wherein the base is an oxide, carbonate, bicarbonate, hydrogen phosphate, hydroxide, alkoxide, or formate or a mixture thereof.

10. A process according to claim 3 wherein the impregnation of step C is carried out to saturation with a salt solution of a metal of Groups IIIb, IVa, IVb, Va, Vb, VIa, VIIIa, Ib or IIb of the Periodic Table.

11. A supported catalyst according to claim 1 wherein said catalytically active metal is palladium.

12. A supported catalyst according to claim 11 wherein said inert support is α-alumina.

13. A support according to claim 1 wherein said metal is iron.

14. A support according to claim 1 wherein said metal is nickel.

15. A support according to claim 1 wherein said metal is cobalt.

16. A support according to claim 1 wherein said metal is manganese.

17. A support according to claim 1 wherein said inert support is impregnated with palladium and iron.

18. A supported catalyst according to claim 1 wherein said metal is a mixture of palladium and nickel.

19. A supported catalyst according to claim 1 wherein said metal is a mixture of palladium and cobalt.

20. A supported catalyst according to claim 1 wherein said metal is a mixture of palladium and manganese.

21. A supported catalyst according to claim 1 wherein said metal comprises a mixture of palladium, copper, and chromium.

22. A supported catalyst according to claim 1 wherein said metal comprises a mixture of palladium and bismuth.

23. A supported catalyst according to claim 1 wherein said metal comprises a mixture of palladium and gold.

24. A supported catalyst according to claim 1 wherein said metal comprises thorium.

25. A supported catalyst according to claim 1 wherein said metal is samarium.

26. A supported catalyst according to claim 1 wherein said metal is titanium.

27. A supported catalyst according to claim 1 wherein said metal is silver.

* * * * *